United States Patent

Nachbur

Patent Number: 4,748,259
Date of Patent: May 31, 1988

[54] PROCESS FOR THE PREPARATION OF MIXTURES OF METAL SALTS OF RING-SUBSTITUTED SALICYLIC ACID COMPOUNDS

[75] Inventor: Hermann Nachbur, Reinach, Switzerland

[73] Assignee: Ciba-Geigy Corporation, Ardsley, N.Y.

[21] Appl. No.: 912,895

[22] Filed: Sep. 26, 1986

[30] Foreign Application Priority Data

Oct. 3, 1985 [CH] Switzerland ............... 4286/85

[51] Int. Cl.$^4$ ............. C07F 3/06; C07F 7/22; C07F 5/06; C07F 9/00
[52] U.S. Cl. .............. 556/132; 556/1; 556/44; 556/49; 556/55; 556/61; 556/106; 556/115; 556/147; 556/189; 562/468
[58] Field of Search ........... 562/468; 556/132, 184, 556/44, 55, 106, 147, 61, 1, 115, 49

[56] References Cited

U.S. PATENT DOCUMENTS

| | | | |
|---|---|---|---|
| 3,035,091 | 5/1962 | Wygant | 526/468 |
| 3,215,727 | 11/1965 | Turk et al. | 562/468 X |
| 3,277,164 | 10/1966 | Haack et al. | 562/468 |
| 3,488,207 | 1/1970 | Vasillades | 556/132 X |
| 3,864,146 | 2/1975 | Oda et al. | 556/132 X |
| 3,871,900 | 3/1975 | Hayashi et al. | 556/132 X |
| 3,924,027 | 12/1975 | Saito et al. | 556/132 X |
| 3,934,070 | 1/1976 | Kimura et al. | 556/132 X |
| 3,983,292 | 9/1976 | Saito et al. | 556/132 X |
| 4,046,941 | 9/1977 | Saito et al. | 556/132 X |

Primary Examiner—Paul F. Shaver

[57] ABSTRACT

Mixtures of a metal salt of formula

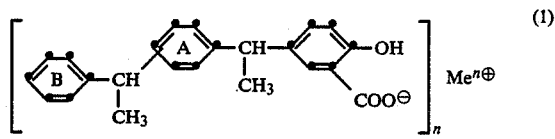

and a metal salt of formula

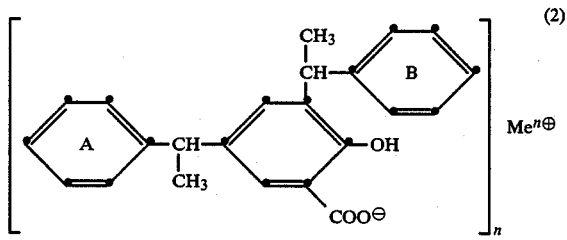

in which formulae (1) and (2)
Me is a metal ion of valency n,
n is 2, 3 or 4, and each of the rings A and B independently of the other is unsubstituted or substituted by halogen, lower alkyl, lower alkoxy or an α-methylbenzyl radical, are prepared by reacting 2 moles of salicylic acid with at least 2 moles of a styrene compound of formula

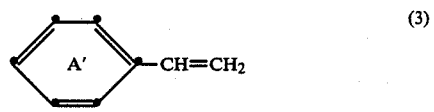

and at least 2 moles of a styrene compound of formula

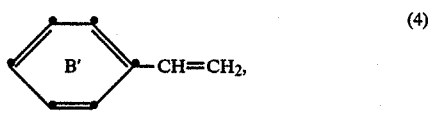

in which formulae (3) and (4) the benzene rings A' and B' are unsubstituted or substituted by halogen, lower alkyl or lower alkoxy, in the presence of an aromatic sulfonic acid, and, in a further step, reacting 2n moles of the resultant mixture of the salicylic acid compound of formula

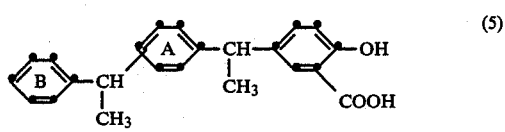

and the salicylic acid compound of formula

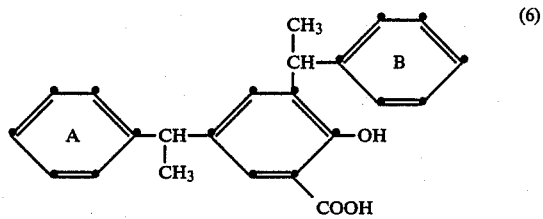

in which formulae (5) and (6) A and B are as defined for formulae (1) and (2), with 2 moles of the salt of an n-valent metal of an inorganic acid or of a lower aliphatic carboxylic acid, where n has the given meaning.

The mixtures of metal salts are particularly suitable for use as color formers in pressure- and heat-sensitive recording materials.

8 Claims, No Drawings

PROCESS FOR THE PREPARATION OF MIXTURES OF METAL SALTS OF RING-SUBSTITUTED SALICYLIC ACID COMPOUNDS

The present invention relates to a process for the preparation of mixtures of metal salts of ring-substituted salicylic acid compounds, which metal salts may be used as developers for colour formers in pressure-sensitive or heat-sensitive recording materials.

Salts of a polyvalent metal and a salicylic acid compound which is disubstituted in positions 3 and 5 are known as acceptors or developers for dyestuff precursors from German Pat. specification No. 2 242 250. α-Methylbenzyl, α,α-dimethylbenzyl and cyclohexyl are mentioned as possible substituents of the salicylic acid. According to this publication, such ring-substituted salicylic acid compounds are prepared from substituted phenols and gaseous carbon dioxide, which substituted phenols are obtained in turn by reacting phenols with e.g. styrene, α-methylstyrene or cyclohexyl chloride.

It has now been found that economically useful mixtures of metal salts of ring-substituted salicylic compounds can be obtained if the salicyclic acid compounds are prepared by reacting salicylic acid with a styrene compound in the molar ratio of 1:2 in the presence of an aromatic sulfonic acid.

Accordingly, the present invention relates to a process for the preparation of a mixture of a metal salt of formula

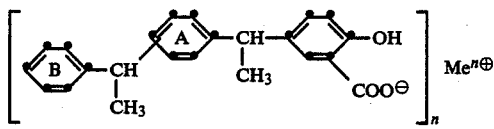
(1)

and a metal salt of formula

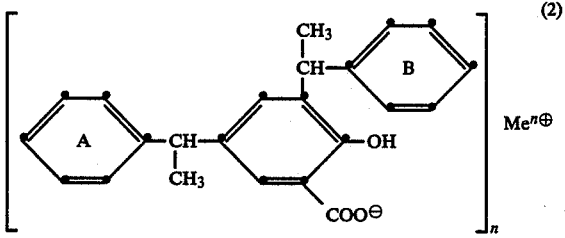
(2)

in which formulae (1) and (2)
Me is a metal ion of valency n,
n is 2, 3 or 4, and
each of the rings A and B independently of the other is unsubstituted or substituted by halogen, lower alkyl, lower alkoxy or an α-methylbenzyl radical.

The process comprises reacting 2 moles of salicylic acid with at least 2 moles of a styrene compound of formula

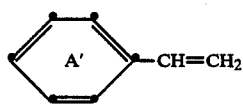
(3)

and at least 2 moles of a styrene compound of formula

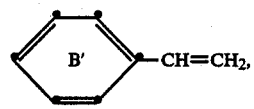
(4)

in which formulae (3) and (4) the benzene rings A' and B' are unsubstituted or substituted by halogen, lower alkyl or lower alkoxy, in the presence of an aromatic sulfonic acid, and, in a further step, reacting 2n moles of the resultant mixture of the salicylic acid compound of formula

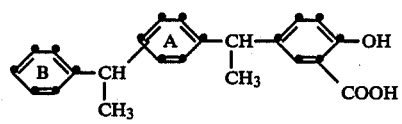
(5)

and the salicylic acid compound of formula

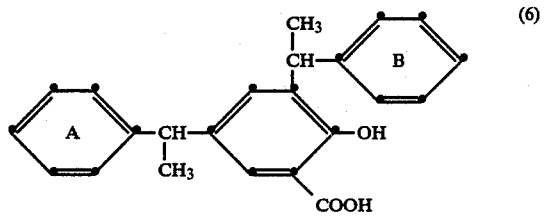
(6)

in which formulae (5) and (6) A and B are as defined for formulae (1) and (2), with 2 moles of the salt of an n-valent metal of an inorganic acid or of a lower aliphatic carboxylic acid, where n has the given meaning.

The mixtures of metal salts prepared by the process of this invention may be obtained in a weight ratio of 9:1 to 1:9.

The salicylate moieties occurring 2 to 4 times in the metal salts of formula (1) and (2) may be identical or different. Preferably they are all identical.

Lower alkyl and lower alkoxy normally denote groups containing 1 to 5, preferably 1 to 3, carbon atoms. Lower alkyl groups may be methyl, ethyl, isopropyl, sec-butyl, tert-butyl, amyl or isoamyl, and lower alkoxy groups may be methoxy, ethoxy, isopropoxy, n-butoxy or tert-butoxy.

Halogen denotes for example fluorine, iodine, bromine or, preferably, chlorine.

The metal salts of this invention are preferably derived from divalent, trivalent or tetravalent metals having an atomic weight from 24 to 210, preferably from 26 to 120. Examples of such metals are aluminium, barium, lead, cadmium, calcium, chromium, iron, gallium, cobalt, copper, magnesium, manganese, molybdenum, nickel, mercury, silver, strontium, tantalum, titanium, vanadium, tungsten, zinc, tin and zirconium. Preferred metals are aluminium, zirconium, vanadium, tin and, in particular, zinc.

The

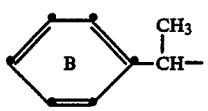

group of the compounds of formulae (1) and (5) is preferably para to the ethylidene group.

The rings A and B are preferably not further substituted. If they do contain substituents, then they are preferably further substituted by halogen, methyl, methoxy or α-methylbenzyl. Each benzene ring A and B may conveniently contain 1 or 2 substituents. The α-methylbenzyl radical is normally present in the ring B.

Interesting mixtures of metal salts which may be used with advantage in the practice of this invention are aluminium salts or, preferably, zinc salts of the substituted salicylic acid compounds of formulae (5) and (6) wherein the ring B is unsubstituted.

The preferred developer is a mixture of the zinc salt of 5-[α-methyl-4'-(α-methylbenzyl)benzyl]salicylic acid and the zinc salt of 3,5-bis[α-methylbenzyl]salicylic acid.

The process for the preparation of the mixture of free salicylic acid compounds of formulae (5) and (6) is conveniently carried out in the temperature range from 20° C. to reflux temperature, preferably from 80° to 150° C.

The reaction time normally depends on the temperature of the reaction medium and is preferably from ½ hour to 5 hours, most preferably from 1 to 3 hours.

The styrene components of formulae (3) and (4) are preferably identical. Representative examples of suitable styrene components are: styrene, p-chlorostyrene, p-methylstyrene, 2,4-dimethylstyrene.

Examples of aromatic sulfonic acids which may suitably be used as catalysts are benzenesulfonic acid, chlorobenzenesulfonic acid, toluenesulfonic acid, chlorotoluenesulfonic acid or xylenesulfonic acid. p-Toluenesulfonic acid is preferred.

The aromatic sulfonic acid, preferably p-toluenesulfonic acid, can be prepared in situ. The preparation of toluenesulfonic acid in situ is described e.g. in Chemical Abstracts, Vol. 79 (1969), 106228r.

When using an aromatic sulfonic acid which has been prepared in situ, it is convenient to carry out the reaction of the salicylic acid with the styrene compounds in an organic solvent that does not participate in the reaction.

Suitable organic solvents employed as reaction medium are cycloaliphatic or, preferably, aromatic hydrocarbons, for example cyclohexane, benzene, toluene or xylene; chlorinated hydrocarbons such as ethylene chloride, tetrachloroethylene, or chlorobenzenes, e.g. chlorobenzene, chlorotoluene or dichlorobenzene; cyclic ethers, e.g. dioxane or tetrahydrofuran; dimethylsulfoxide, or nitriles of aliphatic monocarboxylic acids, e.g. acetonitrile, propionitrile or butyronitrile. Mixtures of these solvents can also be used. Preferred solvents are chlorobenzene, chlorotoluene and, in particular, toluene.

The solvent may be dispensed with if an already prepared aromatic sulfonic acid is employed.

The mixture of the free salicylic acid compounds can be further used direct for the preparation of the metal salts of formulae (1) and (2).

If it is desired to isolate the substituted salicyclic acid compounds of formulae (5) and (6), the acid solution of the reaction product is e.g. first neutralised with aqueous sodium hydroxide solution, and then the neutral solution is acidified with a lower carboxylic acid or an inorganic acid, whereupon the product precipitates in the form of an oil and is isolated. The individual salts can then be separately by chromatography.

The metallisation of the mixture of salicylic acids is conveniently carried out in an alkaline solution of the salicylic acid compounds and preferably in the presence of an alkali, for example a hydroxide, carbonate or bicarbonate of an alkali metal, or ammonium hydroxide, ammonium carbonate or ammonium bicarbonate.

The metallisation can be carried out in the temperature range from 10° to 25° C. In certain cases, and especially when using organic aluminium salts, it is necessary to carry out the reaction at elevated temperature, preferably in the range from 70° to 200° C. However, the reactants can also be reacted in a melt. Suitable fusing assistants are for example salts of lower fatty acids, e.g. sodium acetate, amides of lower fatty acids, e.g. acetamide, and also urea or thiourea or N-substitution products thereof.

As metal donors it is convenient to use the metal salts of mineral acids or carboxylic acids of 1 to 6 carbon atoms, in particular sulfates, halides (chlorides), nitrates, formates, acetates, propionates, oxalates or citrates.

Representative examples of inorganic metal salts are zinc salts such as zinc chloride, zinc sulfate or zinc nitrate, as well as aluminium sulfate, tin dichloride and zirconium oxychloride.

Examples of organic metal salts are zinc diacetate, zinc oxalate, aluminium triisopropylate or aluminium sec-butylate.

Instead of the above zinc salts, it is also possible to use zinc oxide or zinc carbonate, in which case the reaction with the mixture of salicylic acids is preferably carried out in the presence of ammonium formate.

A particularly preferred embodiment of the process for the preparation of the metal compounds of formulae (1) and (2), wherein Me is the zinc ion, comprises adding styrene in portions to a reaction medium consisting of about 1 mole, preferably 1.0 to 1.2 moles, of salicylic acid and p-toluenesulfonic acid, in the temperature range from 100° to 170° C., preferably from 120° to 160° C., and carrying out condensation for 1 to 3 hours. Aqueous sodium hydroxide solution is then added and the alkaline solution is treated with an inorganic zinc salt, preferably zinc chloride, whereupon the resultant mixture of the zinc salts of the corresponding salicylic acid compounds is isolated.

The mixtures of metal salts prepared by the process of this invention are virtually colourless and odourless and are particularly suitable for use as developers for colour formers. They react very readily with conventional colour formers, so that it is possible to obtain spontaneous, stable, non-fading copies. The mixtures of metal salts are preferably used as developers for recording materials which may also be copying materials. The recording material can be pressure- or heat-sensitive.

The colour formers suitable for use in the recording or copying material of this invention are known colourless or faintly coloured compounds which, on coming into contact with the mixture of metal salts of formulae (1) and (2), become coloured or change colour. It is possible to use colour formers, or mixtures thereof, which belong e.g. to the classes of the benzofluoranes, phthalides, azaphthalides, fluoranes, spiropyranes, spirodipyranes, azomethines, quinazolines, leucoauramines, triarylmethaneleuco dyes, carbazolylmethanes, rhodamine lactams, chromenopyrazoles, phenoxazines, phenothiazines, as well as chromeno or chromano colour formers.

Examples of such suitable colour formers are: crystal violet lactone (Registered Trademark), 3,3-(bisaminophenyl)phthalides, 3,3-(bis-substituted indolyl)phthalides, 3-(aminophenyl)-3-indolylphthalides, 3-(aminophenyl)-3-indolylazaphthalides, 6-dialkylamino-2-n-octylaminofluoranes, 6-dialkylamino-2-arylaminofluoranes, e.g. 6-diethylamino-2-(2'-chlorophenylamino)fluorane, 6-dibutylamino-2-(2'-chlorophenylamino)fluorane; 6-dialkylamino-3-methyl-2-arylaminofluoranes, e.g. 2-anilino-3-methyl-6-diethylaminofluorane or 2-(2',4'-dimethylanilino)-3-methyl-6-diethylaminofluorane, 6-dialkylamino-2- or -3-lower alkylfluoranes, 6-dialkylamino-2-dibenzylaminofluoranes, 6-pyrrolidino-2-dibenzylaminofluorane, 6-N-cyclohexyl-N-lower alkyl-3-methyl-2-arylaminofluoranes, 6-pyrrolidino-2-arylaminofluoranes, bis(aminophenyl)furyl-, -phenyl- or -carbazolylmethanes, 3'-phenyl-7-dialkylamino-2',2'-spirodibenzopyranes, bisdialkylaminobenzhydrolalkyl- or -arylsulfinates, benzoyldialkylaminophenothiazines or benzoyldialkylaminophenoxazines.

In the following Preparatory and Use Examples, parts and percentages are by weight unless otherwise stated.

Preparatory Examples

Example 1

With stirring, a mixture of 414 g of salicylic acid and 36 g of p-toluenesulfonic acid.1H₂O is heated to 120° C. to form a partial melt. Then 90 g of styrene are added dropwise over 15 minutes, whereupon the temperature rises to 137° C. and a clear brown solution forms. A further 535 g of styrene are added over 45 minutes, whereupon the reaction temperature rises to 157° C. over 10 minutes and is kept at 150°–157° C. by regulating the rate of dropwise addition. When addition is complete, the reaction mixture is allowed to react for a further 1 hour at 155°–157° C. and is then cooled to 90° C. Then 1595 ml of 2N aqueous sodium hydroxide solution are added and the oily phase of the unreacted styrene, which separates after 2 hours, is removed. The aqueous phase is stirred in a fine stream into a solution of 260 g of zinc chloride in 5 liters of water at a temperature of 10°–15° C. The precipitated zinc salt is isolated by filtration and the filter cake is squeezed out and vacuum dried at 50°–70° C., affording 1031 g of a powdered product which is a mixture of the zinc salt of formula

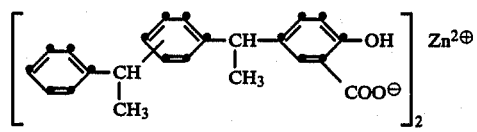

and the zinc salt of formula

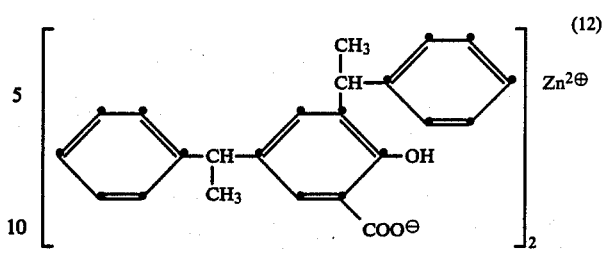

The NMR spectrum of this mixture shows a weight ratio of 1:1. The mixture melts at 104°–118° C.

EXAMPLE 2

The procedure of Example 1 is repeated, replacing the p-toluenesulfonic acid by 36 g of benzenesulfonic acid, to give 1074 g of a powdered product which is a mixture of 30% of the zinc salt of formula (11) and 70% of the zinc salt of formula (12) (NMR spectrum). The mixture melts at 90°–150° C.

EXAMPLE 3

The procedure of Example 1 is repeated, replacing the p-toluenesulfonic acid by 36 g of 2,5-dimethylbenzenesulfonic acid, to give 1077 g of a powdered product which is a mixture of 40% of the zinc salt of formula (11) and 60% of the zinc salt of formula (12) (NMR spectrum). The mixture melts at 60°–110° C.

EXAMPLE 4

(a) With stirring, a mixture of 69 g of salicylic acid and 6 g of p-toluenesulfonic acid.1H₂O is heated to 130° C. to form a partial melt. Then 15 g of styrene are added dropwise over 10 minutes, whereupon the temperature rises to 135° C. and a clear brown solution forms. A further 89.2 g of styrene are added over 35 minutes, whereupon the reaction temperature rises to 155° C. over 10 minutes and is kept at 150°–155° C. by regulating the rate of dropwise addition. When addition is complete, the reaction mixture is allowed to continue to react for a further 1 hour at 155° C. and then cooled to 90° C. Then 265 ml of 2N aqueous sodium hydroxide solution are added and the batch is cooled to 25° C.

Yield: 520 g of a clear brown solution which contains 33% by weight of a 1:1 mixture of the sodium salt of the salicylic acid compounds of formulae (13) and (14):

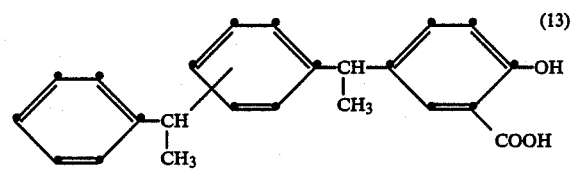

and

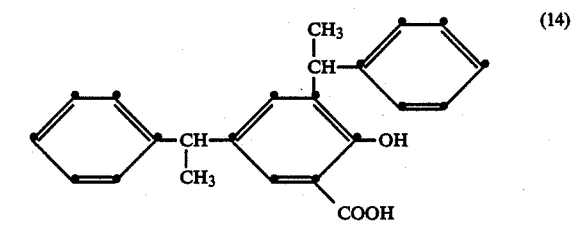

(b) With stirring, 111.5 g of the Na salt solution prepared in (a) are added dropwise at 20° C. to a solution of 15.7 g of zirconyl chloride hexahydrate (ZrOCl$_2$.6H$_2$O) in 150 g of water. Precipitation of the Zr salt is initially only moderate, but is virtually complete after further addition of 250 g of water. The precipitated zirconium salt is isolated by filtration and suspended moist in 100 ml of toluene. After azeotropic removal of water under vacuum at 95° C., the Zr salt is obtained with an H$_2$O content of 0.9%. Yield: 38 g (c. 95% of theory) of a grey powder with a melting point of ~100°–140° C. Analysis: theory Zr=11.43%, found=10.7%.

The product is the zirconium salt of a 1:1 mixture of the compounds of formulae (13) and (14).

EXAMPLE 5

111.5 g of the Na salt solution prepared in Example 4(a) are evaporated to dryness under vacuum at 60° C. The anhydrous salt is dissolved at 20° C. in 100 ml of methanol. With stirring, this solution is then added dropwise at 20° C. to a solution of 10.65 g of tin dichloride in 100 ml of methanol. Virtually no precipitation takes place and the methanol is therefore removed at 60° C. under vacuum. The residue is dissolved in 20° C. in 100 ml of toluene and insoluble constituents are removed by filtration. The toluene is then removed at 95° C. under vacuum, affording 32.8 g (81% of theory) of tin salt, which is in the form of a beige powder at 0° C. and is in semi-solid form at $\geq$30° C. (m.p. c. 30°–50° C.). Analysis: theory Sn=14.66%, found Sn=15.4%.

The product is the tin salt of an approximately 1:1 mixture of the compounds of formulae (13) and (14).

EXAMPLE 6

With stirring, 111.5 g of the Na salt solution prepared in Example 4(a) are added dropwise at 20° C. to a solution of 13.3 g of aluminium sulfate (Al$_2$(SO$_4$)$_2$.18H$_2$O) in 100 g of water. There is distinct precipitation of the Al salt, which is isolated by filtration, suspended in 150 g of water, and again isolated by filtration. The moist product is dissolved in 250 ml of toluene. Azeotropic removal of water under vacuum at 95° C. yields the Al salt containing 2.9% of water.

Yield: 33.6 g (c. 92% of theory, based on anhydrous product) of a beige powder with a melting point of ~60°–85° C. Analysis: theory Al=2.54%, found Al=2.13%.

The product is the aluminium salt of a 1:1 mixture of salicylic acid compounds of formulae (13) and (14).

Use Examples

EXAMPLE 7

Pressure-sensitive recording system

A finely ground aqueous dispersion (2–4 μm) having a 38% solids content and comprising
- 1 part of the mixture of zinc salts obtained in Example 1,
- 7.4 parts of China clay
- 0.8 part of a naphthalenesulfonic acid/formaldehyde condensate, and
- 0.9 part of a styrene/butadiene copolymer (100%), is applied with a doctor blade to coated paper having a weight of 48 g/m$^2$. Coating weight (dry): 6–7 g/m$^2$.

The paper coated with the above receiver layer is placed on a sheet of conventional copying paper (e.g. Zanders) carrying the donor layer, with the coated sides face to face. The donor layer contains a solution of the colour former, e.g. crystal violet lactone, in microcapsules. An intense blue copy is formed after writing by hand or typewriter.

EXAMPLE 8

A finely ground aqueous dispersion (2–4 μm) having a 38% solids content and comprising
- 1 part of the mixture of zinc salts obtained in Example 2,
- 10 parts of China clay
- 0.6 part of polyvinyl alcohol, is applied with a doctor blade to coated paper having a weight of 48 g/m$^2$. Coating weight (dry): 5–6 g/m$^2$.

The paper coated with the above receiver layer is placed on a sheet of conventional copying paper (e.g. Zanders) carrying the donor layer, with the coated sides face to face. The donor layer contains a solution of the colour former, e.g. crystal violet lactone, in microcapsules. An intense blue copy is formed after writing by hand or typewriter.

EXAMPLE 9

A finely ground aqueous dispersion (2–4 μm) having a 38% solids content and comprising
- 1 part of the mixture of zirconium salts obtained in Example 4,
- 10 parts of China clay and
- 0.6 part of polyvinyl alcohol, is applied with a doctor blade to coated paper having a weight of 48 g/m$^2$. Coating weight (dry): 5–6 g/m$^2$.

The paper coated with the above receiver layer is placed on a sheet of conventional copying paper (e.g. Zanders) carrying the donor layer, with the coated sides face to face. The donor layer contains a solution of the colour former, e.g. crystal violet lactone, in microcapsules. An intense blue copy is formed after writing by hand or typewriter.

EXAMPLE 10

A finely ground aqueous dispersion (2–4 μm) having a 38% solids content and comprising
- 1 part of the mixture of aluminium salts obtained in Example 6,
- 10 parts of China clay and
- 0.6 part of polyvinyl alcohol, is applied with a doctor blade to coated paper having a weight of 48 g/m$^2$. Coating weight (dry): 5–6 g/m$^2$.

The paper coated with the above receiver layer is placed on a sheet of conventional copying paper (e.g. Zanders) carrying the donor layer, with the coated sides face to face. The donor layer contains a solution of the colour former, e.g. crystal violet lactone, in microcapsules. An intense blue copy is formed after writing by hand or typewriter.

EXAMPLE 11

0.6 part of the mixture of tin salts obtained in Example 5 are dissolved in 8 parts of toluene and the solution is applied to a coated paper having a surface area of 1 m$^2$ (weight: 48 g/m$^2$). Coating weight (dry): c. 0.6 g/m$^2$.

The paper coated with the above receiver layer is placed on a sheet of conventional copying paper (e.g. Zanders) carrying the donor layer, with the coated sides face to face. The donor layer contains a solution of the colour former, e.g. crystal violet lactone, in microcapsules. An intense blue copy is formed after writing by hand or typewriter.

What is claimed is:

1. A process for the preparation of a mixture of a metal salt of formula

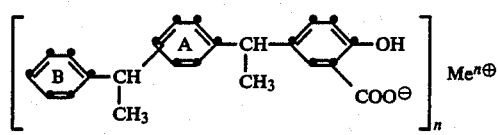

and a metal salt of formula

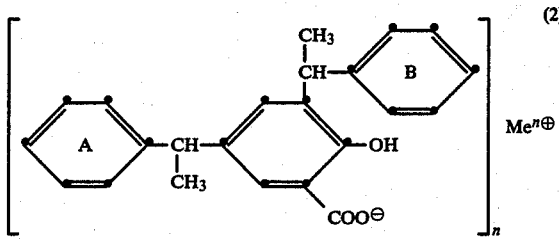

in which formulae (1) and (2)

Me is a metal ion of valency n, selected from the group consisting of aluminium, zirconium, vanadium, tin and zinc, n is 2, 3 or 4, and each of the rings A and B independently of the other is unsubstituted or substituted by halogen, lower alkyl, lower alkoxy or an alpha-methylbenzyl radical, which process comprises treating 2 moles of salicylic acid with at least 2 moles of a styrene compound of formula

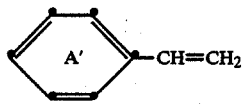

and at least 2 moles of a styrene compound of formula

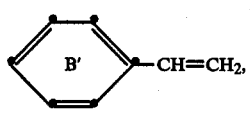

in which formulae (3) and (4) the benzene rings A' and B' are unsubstituted or substituted by halogen, lower alkyl or lower alkoxy, at a temperature in the range of 80° to 170° C., in the presence of an aromatic sulfonic acid, and, in a further step, reacting 2n moles of the resultant mixture of the salicylic acid compound of formula

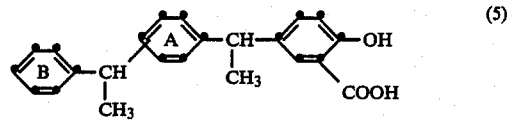

and the salicylic acid compound of formula

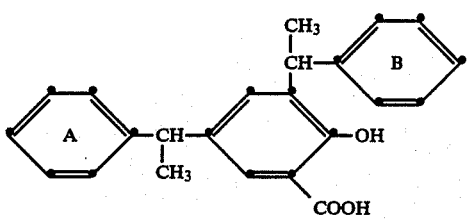

in which formulae (5) and (6) A and B are as defined for formulae (1) and (2), with 2 moles of the salt of an n-valent metal of an inorganic acid or of a lower aliphatic carboxylic acid, where n has the given meaning.

2. A process according to claim 1, wherein the rings A and B are unsubstituted.

3. A process according to claim 1, wherein the ring B is unsubstituted or substituted by α-methylbenzyl.

4. A process according to claim 1, wherein the product is a mixture of the zinc salt of 5-[α-methyl-4'-(α-methylbenzyl)benzyl]salicylic acid and the zinc salt of 3,5-bis[α-methylbenzyl]salicylic acid.

5. A process according to claim 1, wherein the metal salt components of the mixture are in the weight ratio of 1:9 to 9:1.

6. A process according to claim 1, wherein the aromatic sulfonic acid is p-toluenesulfonic acid.

7. A process according to claim 1, wherein the aromatic sulfonic acid is toluenesulfonic acid which is prepared in situ.

8. A process according to claim 1, wherein sytrene is condensed with salicylic acid in the presence of p-toluenesulfonic acid at a temperature of 100° to 170° C., and the resultant mixture of the salicylic acid compound of formula

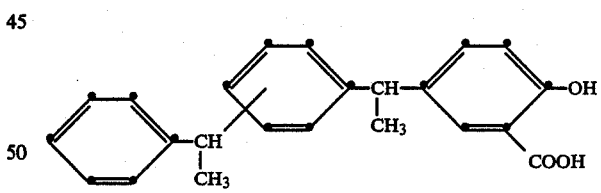

and the salicylic acid compound of formula

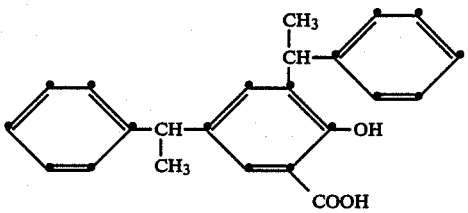

is reacted with zinc chloride.